United States Patent [19]

Bailey et al.

[11] Patent Number: 5,180,807
[45] Date of Patent: Jan. 19, 1993

[54] C-TERMINAL PEPTIDE OR PROTEIN SEQUENCING REAGENT AND METHOD

[75] Inventors: Jerome M. Bailey, Duarte; John E. Shively, Arcadia, both of Calif.

[73] Assignee: City of Hope, Duarte, Calif.

[21] Appl. No.: 801,944

[22] Filed: Dec. 3, 1991

[51] Int. Cl.⁵ .................. G01N 33/68; C07K 1/00; C07K 1/08
[52] U.S. Cl. .................. 530/345; 436/89; 436/161; 530/402; 530/427
[58] Field of Search .................. 530/345, 402, 427; 436/89, 161

[56] References Cited

U.S. PATENT DOCUMENTS 4,837,165  6/1989  Hawke .................. 436/89
5,041,388  8/1991  Boyd et al. .................. 436/89
5,049,507  9/1991  Hawke et al. .................. 436/89

OTHER PUBLICATIONS

Kenner et al., J. Chem. Soc. 673-678 (1953).

Primary Examiner—Howard E. Schain
Attorney, Agent, or Firm—Edward S. Irons

[57] ABSTRACT

A carboxy terminal protein sequencing process is disclosed which utilizes phosphoroisothiocyanatidate for the derivatization step.

14 Claims, 1 Drawing Sheet

C-TERMINAL PEPTIDE OR PROTEIN SEQUENCING REAGENT AND METHOD

FIELD OF THE INVENTION

This invention relates to a novel reagent and method for the carboxy-terminal sequencing of polypeptides.

BACKGROUND OF THE INVENTION

A The Prior Art

The large number of cloned gene products and the widespread use of DNA sequencing to determine the primary structure of proteins, has increased the need for carboxy-terminal (C-terminal) sequencing to better define post synthetic processing of proteins. C-terminal sequencing complements existing N-terminal degradations based on Edman chemistry (Edman, P. *Acta. Chem. Scand.* 4:283-293 (1950)). Although many methods have been proposed (see Rangarajan, M., Chemical methods of amino acid sequence analysis from carboxy terminal end. In Protein/Peptide sequence Analysis: Current Methodologies (Brown, A.S., Ed.) pp. 135-144, CRC Press, Bora Raton, Florida (1988) and Ward, C.W., Carboxyl terminal sequence analysis. In Practical Protein Chemistry——A Handbook (Darbre, A., Ed.) pp. 491-525, John Wiley and Sons, Ltd. (1986)) the thiocyanate method, first described by Schlack and Kumpf, *Z. Physiol. Chem.* 154:125-170 (1926), has been the most widely studied and the most attractive because of its similarity to the Edman degradation. This method involves reaction of a protein or peptide with isothiocyanate reagents, in the presence of acetic anhydride, to form a C-terminal thiohydantoin amino acid. The derivatized amino acid is then hydrolyzed to yield a shortened polypeptide and a thiohydantoin amino acid. As the thiohydantoin amino acids have similar UV absorption spectra and equivalent extinction coefficients as the phenylthiohydantoin amino acids formed during the Edman degradation, the sensitivity of the thiocyanate method is expected to be similar to that of current N—terminal methods (10-200 pmol, 20-30 cycles). Historically, the main disadvantages of this procedure have been the severity of the conditions required for complete derivatization of the C-terminal amino acid and for hydrolysis of the derivatized amino acid to yield a shortened peptide and thiohydantoin derivative. Although several groups have tried to reduce the severity of the hydrolysis conditions (Waley, et al. *J. Chem. Soc.* 1951:2394-2397 (1951); Kjaer, et al. *Acta Chem. Scand.* 6:448-450 (1952); Turner, et al. *Biochim. Biophys. Acta.* 13:553-559 (1954), it was not until the introduction of acetohydroxamate (Stark, G.R. *Biochemistry* 7:1796-1807 (1968) as a mild and rapid cleavage reagent, that the hydrolysis problem appeared solved. The introduction of trimethylsilylisothiocyanate (TMS—ITC) (see U.S. Pat. No. 4,837,165) improved the yield of thiohydantoin formation and reduced the number of complicating side products. However, even with these improvements the repetitive yields were low, limiting the number of degradation cycles to 2 or 3 residues, and certain amino acids were reported to be unable to form thiohydantoins (Hawke, et al. *Anal. Biochem.* 166:298-307 (1987); Miller, et al., Techniques in Protein Chemistry (Hugli, T.E., Ed.) pp. 67-78, Academic Press, Inc. (1989)).

Recent work, Bailey, et al. *Biochemistry* 29:3145-3156 (1990), found that hydrolysis with acetohydroxamate led to the formation of a shortened peptide with a stable hydroxamate ester at the C-terminus, thereby preventing further degradation and explaining the low repetitive yields obtained with this reagent (Miller, supra; Meuth, et al., *Biochem.* 21:3750-3757 (1982)). Hydrolysis with dilute aqueous triethylamine was found to lead to the quantitative formation of a thiohydantoin amino acid and a shortened peptide capable of continued degradation. Additional work (Bailey, supra) addressed the generality of the thiocyanate method by examining the reaction of TMS—ITC with model peptides containing most of the naturally occurring amino acids. Problems were identified when Pro, Asp, Glu, Thr, and Asn were encountered during the degradation. Minimization of the reaction time with acetic anhydride was found to allow the quantitative degradation of Glu and Thr and addition of a nucleophile prior to derivatization by TMS—ITC was used to allow partial degradation of C-terminal Asp.

Automation of C-terminal chemistry has been attempted by several groups Application of this chemistry to the solid phase (polypeptides covalently attached to a solid support) has been recognized to facilitate the successful automation of this chemistry. The advantages of covalently immobilizing polypeptide to a solid support include: elimination of sample washout thereby resulting in high initial and repetitive yields, the ability to use reagents and solvents optimal for derivatization and washing, and the ability to efficiently wash the sample to remove reaction by—products resulting from thiohydantoin formation, thereby creating a potential for a low chemical background.

The concept of solid phase sequencing for N—terminal Edman chemistry was first proposed by Laursen, R.A. *Eur. J. Biochem* 20:89-102 (1971), and has since been used successfully by a number of groups for the Edman degradation (Laursen, et al. *FEBS Lett.* 21:67-70 (1972); L,Italien, et al. *Anal. Biochem.* 127:198-212 (1982); L,Italien, Methods in Protein Microcharacterization, (Shively, J.E., Ed.) pp. 279-314, Humana press, Inc. (1986)). Initial attempts at C-terminal sequencing using the thiocyanate chemistry from covalently attached peptides was made by several groups. Williams, et al. *FEBS Lett.* 54:353-357 (1975) were able to perform 1-3 cycles on peptides (1 $\mu$) covalently attached to N—hydroxysuccinimide activated glass beads using 12 N HCl for cleavage of the peptidylthiohydantoins. Utilizing this same procedure, Rangarajan, et al. *Biochem. J.* 157:307-316 (1976) were able to perform six cycles on ribonuclease (1 $\mu$) covalently coupled to glass beads with a cycle time of 5 to 6 hours. Three successful cycles, with HPLC identification of the released amino acid thiohydantoins, were performed by Meuth et al. *Biochem.* 21:3750-3757 (1982) on a 22—amino acid polypeptide (350 nmol) covalently linked to carbonyldiimidazole activated aminopropyl glass. These authors used thiocyanic acid for derivatization to a peptidylthiohydantoin and acetohydroxamate for cleavage further reducing the time per cycle to 3 hours. A more recent report by Inglis et al., Methods in Protein Sequence Analysis (Wittmann—Lebold, B., Ed.) pp. 137-144, Springer—Verlag (1989) reports the sequential degradation of nine residues from a synthetic decapeptide (30 nmol) covalently coupled to glass beads with a cycle time of 48 min., however no experimental details were given.

Applicants initial work concerning the automation of the thiocyanate chemistry for the purpose of carboxy—terminal sequencing of proteins and peptides revealed several problems: (1) cleavage of the peptidylthiohydantoin with acetohydroxamate resulted in a shortened peptide blocked to further sequence degradation from the C-terminus due to the formation of a stable hydroxamate ester, (2) although cleavage of the peptidylthiohydantoin with dilute aqueous triethylamine does not result in the formation of a blocked shortened peptide, the use of aqueous solutions on peptides covalently bound to polyvinyldifluoride (PVDF) was found to inadequately "wet" the support and cleavage did not occur (50° C.) or only very slowly at elevated temperatures (70° C.). The inclusion of 30% water miscible organic solvent to the dilute triethylamine solution was found to allow adequate "wetting" of the membrane support, but significantly inhibited the cleavage reaction (Bailey, et al., Carboxy terminal sequencing: Automation and application to the solid phase, Techniques in Protein Chemistry: II (Villafranca, J.J., Ed.) pp. 115-129, Academic Press, Inc. (1991), (3) the activation of the C-terminal carboxylic acid with acetic anhydride was found to prevent or contribute to the reduced yields of sequencing on certain of the twenty naturally occurring amino acids (Bailey, et al., supra (1990), e.g., threonine, serine, aspartate, glutamate, and proline.

The cleavage problems were solved with the introduction of a new reagent, sodium trimethylsilanolate, for cleavage of the covalently coupled peptidylthiohydantoins and the introduction of a carboxylic acid modified polyethylene support for covalent attachment of the peptide sample (see, e.g., patent application PCT/US90/02723). This novel cleavage reagent was found to hydrolyze specifically the peptidylthiohydantoin into a shortened peptide capable of continued sequencing from the C-terminus and a thiohydantoin amino acid. The thiohydantoin amino acids are then identified by HPLC.

B. Derivatization of the C—Terminal Amino Acid

The thiocyanate chemistry for C-terminal sequencing can be thought of as consisting of two separate parts, (1) the derivatization of the C-terminal amino acid to form a thiohydantoin, and (2) the specific cleavage of that c—terminal thiohydantoin to form a shortened peptide capable of continuing degradation and a thiohydantoin amino acid.

Although the derivatization of amino acids to the corresponding thiohydantoins has been studied since this reaction was first reported in 1911 (Johnson, et al. *J. Am. Chem. Soc.* 33:1973-1978 (1911)), the mechanism of peptidylthiohydantoin formation by acetic anhydride and thiocyanate ions is still not well understood. Early experiments confirmed the assumption that thiocyanic acid is first formed when acetic anhydride and acetic acid interact with ammonium thiocyanate and it is the thiocyanic acid which actually reacts to form the thiohydantoin (Johnson, et al., *J. Am. Chem. Soc.* 35:1136-1143 (1913)). The differing ability of the various salts of thiocyanic acid to form a thiohydantoin was reasoned to result from their ability to form thiocyanic acid on interaction with acetic anhydride and acetic acid (Johnson, et al. J. Am. Chem. Soc. 37:2406-2416 (1915). When more convenient methods for the preparation of thiocyanic acid became available, thiocyanic acid, in the presence of acetic anhydride, was found to be more reactive for the formation of 2—thiohydantoins than were the thiocyanate salts. As a result, thiocyanic acid has been used by Kubo, et al., *Chem. Pharm. Bull.* 19:210-211 (1971) and more recently by Inglis, et al., supra (1989) for the sequential degradation of peptides from the C-terminus. However, one of the principal drawbacks of thiocyanic acid is that it tends to be self reactive, even at ambient temperature, and quickly loses its ability to derivatize the peptide. Furthermore, these polymeric thiocyanic acid products are intensely UV absorbing at the wavelengths used for thiohydantoin detection and can subsequently interfere with the HPLC identification of the released thiohydantoin amino acid. The instability of the free thiocyanic acid presents difficulties when the chemistry is automated, which requires reagents stable to storage in a reagent bottle at room temperature. As discussed by Inglis, et al., C-terminal sequence analysis, Met. Protein Sequence Analysis (Jornvall/Hoog/Gustavsson, Eds.) pp. 23-34, Birkhauser-Verlag, Basel (1991), one way to facilitate stabilization of the thiocyanic acid is to refrigerate it while in the automated instrument. A less costly and more convenient solution to the problems caused by the use of thiocyanic acid involves the use of trimethylsilylisothiocyanate (TMS-ITC) for derivatization of the C-terminal amino acid to a thiohydantoin (see, U.S. Pat. No. 4,837,165). Consistent with the observation that silylated amines have often been found to be better nucleophiles than the corresponding unsubstituted amines (Fleming, I., Comprehensive Organic Chemistry, Vol. 3 (Jónes, D.N., Ed.) pp. 541-686, Pergamon Press (1979)), the trimethylsilyl group offered two advantages, (1) it stabilized the thiocyanate sufficiently so that self-reaction was no longer a problem, and (2) it did not compromise the ability of the thiocyanate to form thiohydantoins.

The intermediate involved in thiohydantoin formation has been a subject of study for many years. An oxazolinone was postulated to be a necessary intermediate during the synthesis of amino acid thiohydantoins with acetic anhydride and ammonium thiocyanate when this reaction was first studied (Johnson, et al., *J. Am. Chem. Soc.* 35:1136-1143 (1913)). The racemization of the C-terminal amino acids observed on reaction with acetic anhydride and TMS-ITC (Bailey supra (1990)) suggests that reaction of peptides with acetic anhydride forms a peptide oxazolinone. This is consistent with the above postulated mechanism. The formation of oxazolinones is known to cause racemization of amino acids (Csonka, et al. *J. Biol. Chem.* 99:213-216 (1933); Carter, et al., *J. Biol. Chem.* 133:117-128 (1940); Goodman, et al. *J. Am. Chem Soc.* 86:2918-2922 (1964)). Further evidence of a oxazolinone intermediate during the formation of amino acid thiohydantoins was obtained by Csonka, et al. supra. Additional studies described by Cornforth, J.W., The Chemistry of Penicillin, pp. 688-848, Princeton University Press (1949) actually demonstrated the formation of an oxazolinone intermediate in the formation of thiohydantoins by the combined use of absorption spectra and polarimetry to follow the rate of oxazolinone formation. In fact, once the oxazolinone was formed, the reaction with isothiocyanic acid was found to be facile enough to occur readily at 0° C. in the case of 2-phenyl-4-benzly-5-oxazolinone (Cornforth (1949), supra).

Activation of th carboxylic acid is typically done in the presence of the thiocyanate reagent. Acetic anhydride, first used by Johnson and Nicolet (1911), supra, has been the most commonly used reagent and is still the reagent o choice. Propionic anhydride was also found to be as effective as acetic anhydride for activation, while benzoic anhydride was found to be uneffective (Johnson, supra, (1915)). Kubo, et al. *Chem. Pharm. Bull.* 19:210–211 (1971) also found acetyl chloride to be effective for activation. Woodward's reagent K (Woodward, et al. *Tetrahedron, Suppl.* 7:415–440 (1986)) was recently shown to be an effective activating agent (Hawke, et al., *Tetrahedron Letters* 31:3849–3852 (1990)). Dicyclohexylcarbodiimide was also shown by applicants to be capable of forming an activated carboxylic group suitable for reaction with TMS-ITC to form a thiohydantoin in good yield. The commo link between all of these activating reagents is that they are all capable of forming an oxazolinone on the C-terminus of a protein or peptide.

Recent work examined the reaction of acetic anhydride and TMS-ITC with model peptides containing most of the naturally occurring amino acids at the C-terminus (Bailey, et al., supra (1990)). It was found that the reaction between acetic anhydride and TMS-ITC could be separated and each step performed independent of the other. Problems were identified with glutamate, aspartate, threonine, and proline. All of these problems occurred on the activation step with acetic anhydride. Both glutamate and apartate rapidly form a cyclic anhydride in the presence of acetic anhydride which is not reactive with TMS-ITC or the thiocyanate salts In the case of glutamate, the kinetically favored 5-membered oxazolinone ring, capable of reaction with TMS-ITC, initially forms, but is rapidly converted into the more thermodynamically stable 6-membered cyclic anhydride which is not capable of reaction with TMS-ITC. Because the oxazolinone is initially formed, a minimum reaction time with acetic anhydride can make possible up to 80% derivatization of C-terminal glutamate to a thiohydantoin (Bailey, et al., supra (1990)).

Formation of the cyclic anhydride in the case of C-terminal aspartic acid is so rapid that no formation of thiohydantoin aspartate could be detected during manual solution phase sequencing (Bailey, et al., supra (1990)). Aspartate is known to form a cyclic anhydride which is not reactive to thiocyanate on reaction with acetic anhydride (Nicolet, B.H., *J.Amer. Chem. Soc.* 52:1192–1195 (1930); Swan, J.M. *Nature* 169:826–828 (1952); Barker, C.C., *J. Chem. Soc.* 453–456 (1953); Stark, G.R. *Biochemistry* 7:1796–1807 (1968)).

It is postulated that the formation of the oxazolinone of C-terminal aspartate, required for thiohydantoin formation, is the initially favored reaction with acetic anhydride, but once formed, rapidly rearranges to the more thermodynamically stable five-membered cyclic anhydride which is not capable of reaction with TMS-ITC. Threonine on reaction with acetic anhydride readily forms an oxazolinone which is capable of reaction with TMS-ITC to form a thiohydantoin, but this oxazolinone can readily dehydrate at its side chain hydroxyl group to form an unsaturated oxazolinone, which is not capable of reaction with TMS-ITC. Proline due to its tertiary amino group, is not capable of forming an oxazolinone (Matsuo, et al., *Biochem. Biophys. Res. Comm.* 22:69–74 (1966); Holcomb, et al. *Biochemistry* 4:1291–1296 (1968)), so any reaction with TMS-ITC would have to be through a linear mixed anhydride intermediate. The fact that TMS-ITC does not react with the cyclic anhydride formed when aspartic acid is at the C-terminus of a peptide (Bailey, supra (1990)), suggests that TMS-ITC may not be able to react with the mixed anhydride formed when proline is at the C-terminus.

An isothiocyanate reagent capable of specific reaction with the carboxylic acid at the C-terminus of a protein or peptide in the absence of activation with acetic anhydride would provide a means to solve some of the problems outlined above. In particular, such a reagent would potentially be able to improve the yields obtained when amino acids such as glutamate, aspartate, threonine, or proline are encountered in a sequential degradation from the C-terminus of a protein or peptide. Such a reagent is phosphoroisothiocyanatidate. This reagent was first synthesized and proposed (as diphenyl phosphorisothiocyanatidate) for use in C-terminal sequencing by Kenner, et al. *J. Chem. Soc.* 673–678 (1953). The main drawback is its slow reaction time to form a thiohydantoin amino acid. As shown by Kenner, et al., this reagent in the presence of triethylamine takes 110 hours to quantitatively form a thiohydantoin amino acid.

SUMMARY OF THE INVENTION

This invention provides, as a novel C-terminal sequencing reagent, a combination of phosphoroisothiocyanatidate and pyridine.

With the inclusion of pyridine in an amount in slight excess to the concentration of the phosphoroisothiocyanatidate reagent, the reaction proceeds to completion in under one hour. This much shortened reaction time permits derivatization of the C-terminal amino acid to a thiohydantoin in a comparable amount of time to that observed with trimethylsilyl isothiocyanate (Bailey, supra (1990)), the reagent currently used for C-terminal sequencing. The sequence of reactions proposed for automated C-terminal sequencing with the phosphoroisothiocyanatidate reagent are shown in FIG. 1. The polypeptide to be sequenced is first covalently coupled to a solid support, preferably carboxylic acid modified polyethylene. The covalently coupled peptide is then reacted for 30–40 minutes with a solution of phosphoroisothiocyanatidate and pyridine (present in slight molar excess to phosphoroisothiocyanatidate) at 50° C. the peptide is then rinsed with excess acetonitrile and the derivatized C-terminal amino acid is specifically cleaved with sodium trimethylsilanolate in a 50% methanol/tert-butanol solution. The released thiohydantoin amino acid is then identified by reverse phase HPLC.

DETAILED DESCRIPTION OF THE INVENTION

Figure 1:
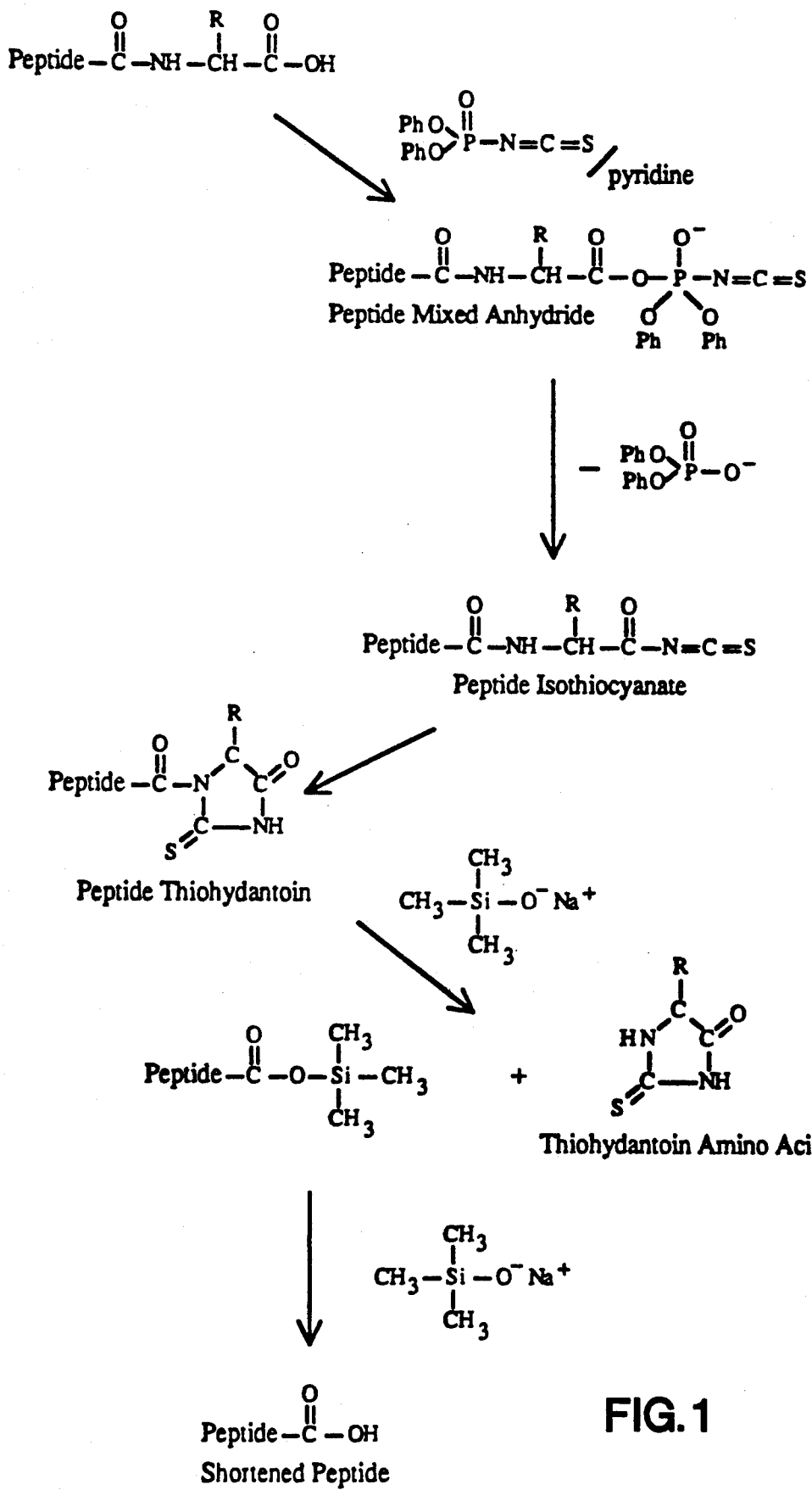
FIG. 1 illustrates one series of reactions for C-terminal sequencing with the novel reagents of this invention.

The novel C-terminal sequencing reagent of the invention is preferably utilized in solution in a polar inert solvent such as acetonitrile.

The molar ratio of phosphoroisothiocyanatidate t pyridine may be within the range of from about 0.5 to about 10. Preferably, the pyridine is present in a greater concentration than the phosphoroisothiocyanatidate. A mol ratio of phosphoroisothiocyanatidate to pyridine of from about 1.0 to about 2.0 is preferred.

The polypeptide sample may be covalently coupled to a solid support, preferably carboxylic acid modified polyethylene as described in patent application PCT/US91/04434 and U.S. application No. 07/576,943.

The peptide, preferably covalently coupled is reacted with the phosphoroisothiocyanatidate-pyridine reagent at a temperature of from about 20° C. to about 90° C, preferably about 50° C. for a time period of from about 5 to 90 minutes, preferably about 40 minutes.

The derivatized peptide is preferably rinsed with the reagent solvent, e.g., acetonitrile. Cleavage of the thiohydantoin amino acid may be accomplished by various procedures known to the art.

In the preferred practice of the invention, specific cleavage is accomplished with sodium trimethylsilanolate in a 50% by volume methanol-butanol solution as described in patent application PCT/US91/04434. The released thiohydantoin amino acid is identified by reverse phase HPLC.

The C-terminal phosphoroisothiocyanatidate derivatization reaction is understood to proceed through the concerted mechanism illustrated by FIG. 1. Referring to the figure, pyridine catalyzes removal of the phosphoryl moiety to generate a linear acyl isothiocyanate which then cyclizes to the thiohydantoin.

The use of phosphoroisothiocyanatidate in the presence of excess triethylamine, as originally described by Kenner, et al., (1953), supra, instead of pyridine as described above, in a 40 minute reaction with the tripeptide, Thr-Val-Leu, at 50° C. resulted in no formation of the peptidyl thiohydantoin. While the reaction conducted in the presence of pyridine provided the expected peptidylthiohydantoin in good yield. Further evidence of the FIG. 1 mechanism is that only a single peptidylthiohydantoin was formed by reaction with phosphoroisothiocyanatidate, whereas the reaction with acetic anhydride and trimethylsilyl isothiocyanate is well known to form two diastereomeric peptidylthiohydantoins (Bailey, (1990), supra).

EXAMPLE I

Solution phase C-terminal analysis of Thr-Val-Leu

Thr-Val-Leu (60 nmol), N-protected with an acetyl group, was reacted with phosphoroisothiocyanatidate (0.06 μ), pyridine (0.12 μ) in acetonitrile for 40 minutes at 50° C. The total reaction volume was 0.1 ml. At the end of the reaction period the peptide solution was dried in a vacuum centrifuge and analyzed by reverse HPLC as described by Bailey, supra (1990). A single peptidyl thiohydantoin peak was found. This was confirmed by FAB/MS. This peak had the expected $MH_+$ ion of 415. The peptidyl thiohydantoin was then cleaved with dilute aqueous triethylamine for 10 minutes as described by Bailey, supra (1990). The C-terminal amino acid was identified as leucine by reverse phase HPLC and comparison to thiohydantoin leucine standards.

EXAMPLE II

C-Terminal Analysis of Thr-Val-Leu Covalently Attached to Carboxylic Acid Modified Polyethylene A sample of Thr-Val-Leu is covalently attached to an activated, carboxylic acid modified support of the kind and in the manner described in patent application PCT/US91/04434.

The covalently coupled peptide is reacted for about 40 minutes at a temperature of about 50° C. with a acetonitrile solution of about 0.008 mol. of phosphoroisothiocyanatidate and about 0.0125 mol of pyridine. The derivatized peptide is rinsed with acetonitrile and the C-terminal thiohydantoin amino acid is specifically cleaved with sodium trimethylsilanolate in a 50% by volume methanol t-butanol solution.

The use of phosphoroisothiocyanatidate in the presence of pyridine for C-terminal sequencing provides a number of advantages over the use of isothiocyanate salts in the presence of acetic anhydride. These include: (1) milder reaction conditions, (2) elimination of the acetic anhydride activation step, thereby potentially improving the yields with Thr, Glu and Asp, (3) elimination of the racemization caused by the requisite oxazolinone formation in the acetic anhydride/thiocyanate chemistry, and (4) improvement in the sequencing yields of protein samples, since most proteins are not soluble in acetic anhydride.

The exemplification of the invention describes the use of pyridine in solution in isothiocyanate. The invention also includes the derivatization of polypeptides by phosphoroisothocyanatidate in pyridine per se. In addition, the pyridine ring may be substituted, for example by alkyl groups having from about 1 to about 5 carbon atoms or with halogen atoms such as chlorine, bromine, fluorine and iodine atoms or a combination thereof.

The invention specifically includes, in addition to the exemplified phosphoroisothocyanatidate agent a diphenyl, diethyl and similar analogs. The diphenyl and diethyl reagents are illustrated by the following formula:

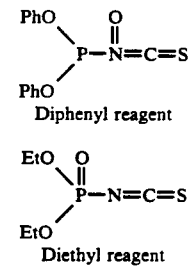

Diphenyl reagent

Diethyl reagent

We claim:

1. In a process for the carboxy terminal sequencing of a polypeptide which involves the reaction of said protein or peptide with an isothiocyanate reagent to for a carboxy-terminal thiohydantoin amino acid, the improvement which comprises utilizing as said isothiocyanate reagent, a combination of phosphoroisothiocyanatidate and pyridine.

2. A process as defined by claim 1 in which said pyridine is present in said combination in molar excess with respect to said phosphoroisothiocyanatidate.

3. A process as defined by claim 1 or claim 2 in which said combination of phosphoroisothiocyanatidate and pyridine is in solution in an inert polar solvent.

4. A process as defined by claim 1 or claim 2 in which said combination of phosphoroisothiocyanatidate and pyridine is in solution in acetonitrile.

5. A process as defined by claim 1 in which said protein or peptide is covalently attached to a solid support.

6. A process as defined by claim 5 in which said solid support is an activated, carboxylic acid modified, polyethylene support.

7. A process for the carboxy terminal sequencing of a protein or peptide sample which comprises
   (i) reacting said sample with a reagent consisting essentially of phosphoroisothiocyanatidate and pyridine to form a thiohydantoin derivative of the carboxy terminal amino acid thereof, and (ii) reacting said derivatized sample with sodium trimethylsilanolate to release a thiohydantoin amino acid.

8. A process as defined by claim 7 in which in the reagent of step (i), the pyridine is present in molar excess with respect to the phosphoroisothiocyanatidate.

9. A process as defined by claim 7 or claim 8 in which said sample is covalently attached to a solid support.

10. A process as defined by claim 7 or 8 in which said sample is covalently attached to a carboxylic acid modified polyethylene support.

11. In a process for the carboxy terminal sequencing of a polypeptide in which a thiohydantoin derivative of the carboxy terminal amino acid of said polypeptide is formed and said derivative is then cleaved to release a thiohydantoin amino acid, the improvement which comprises reacting said carboxy terminal amino acid with a mixture of phosphoroisothiocyanatidate and pyridine to form said thiohydantoin derivative.

12. A process as defined by claim 11 in which said mixture contains pyridine in an amount in slight excess to said phosphoroisothiocyanatidate.

13. A process as defined by claim 11 in which the molar ratio of phosphoroisothiocyanatidate to pyridine in said mixture is from about 0.05 to 10.

14. A process as defined by claim 11 in which the molar ratio of phosphoroisothiocyanatidate to pyridine in said mixture is from about 1.0 to 2.0.

* * * * *

UNITED STATES PATENT AND TRADEMARK OFFICE
CERTIFICATE OF CORRECTION

PATENT NO. : 5,180,807

DATED : January 19, 1993

INVENTOR(S) : Jerome M. Bailey and John E. Shively

It is certified that error appears in the above-identified patent and that said Letters Patent is hereby corrected as shown below:

Column 8, line 42, delete "pro-".
line 43, delete "tein or peptide" and insert --polypeptide--.
line 43, delete "for" and insert --form--.
line 46, after "of", insert --diphenyl--.
line 57, delete "pro-".
line 58, delete "tein or peptide" and insert --polypeptide--.
line 63, delete "protein or peptide" and insert --polypeptide--.
line 65, after "of", insert --diphenyl--.

Signed and Sealed this

Thirty-first Day of October 1995

Attest:

BRUCE LEHMAN

Attesting Officer    Commissioner of Patents and Trademarks